United States Patent
Han

(10) Patent No.: US 11,896,630 B2
(45) Date of Patent: *Feb. 13, 2024

(54) COMPOSITION FOR A FORMULATED ORAL PREBIOTIC EDIBLE COMPOSITION

(71) Applicant: Knoze Jr. Corporation, Los Alamos, NM (US)

(72) Inventor: Shunsheng Han, Los Alamos, NM (US)

(73) Assignee: Knoze Jr. Corporation

( * ) Notice: Subject to any disclaimer, the term of this patent is extended or adjusted under 35 U.S.C. 154(b) by 300 days.

This patent is subject to a terminal disclaimer.

(21) Appl. No.: 17/376,237

(22) Filed: Jul. 15, 2021

(65) Prior Publication Data

US 2021/0338747 A1    Nov. 4, 2021

Related U.S. Application Data

(63) Continuation-in-part of application No. 16/519,909, filed on Jul. 23, 2019, now Pat. No. 11,083,760, which is a continuation-in-part of application No. 15/706,323, filed on Sep. 15, 2017, now Pat. No. 10,398,670, which is a continuation-in-part of application No. 15/495,188, filed on Apr. 24, 2017, now Pat. No. 9,795,579.

(51) Int. Cl.

| | |
|---|---|
| *A61K 35/744* | (2015.01) |
| *A61K 31/198* | (2006.01) |
| *A61K 47/26* | (2006.01) |
| *A61K 47/46* | (2006.01) |
| *A61K 47/44* | (2017.01) |
| *A61K 33/06* | (2006.01) |
| *A23L 33/00* | (2016.01) |
| *A23L 33/175* | (2016.01) |
| *A23L 33/125* | (2016.01) |
| *A23L 33/135* | (2016.01) |
| *A23L 33/12* | (2016.01) |
| *A23L 33/105* | (2016.01) |
| *A23G 3/36* | (2006.01) |
| *A23G 3/40* | (2006.01) |
| *A23G 3/42* | (2006.01) |
| *A23G 3/44* | (2006.01) |
| *A23G 3/48* | (2006.01) |
| *A23G 3/56* | (2006.01) |
| *A23G 1/36* | (2006.01) |
| *A23G 1/40* | (2006.01) |
| *A23G 1/42* | (2006.01) |
| *A23G 1/44* | (2006.01) |
| *A23G 1/48* | (2006.01) |
| *A61K 9/00* | (2006.01) |

(52) U.S. Cl.
CPC .............. *A61K 35/744* (2013.01); *A23G 1/36* (2013.01); *A23G 1/40* (2013.01); *A23G 1/423* (2013.01); *A23G 1/44* (2013.01); *A23G 1/48* (2013.01); *A23G 3/366* (2013.01); *A23G 3/40* (2013.01); *A23G 3/42* (2013.01); *A23G 3/44* (2013.01); *A23G 3/48* (2013.01); *A23G 3/563* (2013.01); *A23L 33/105* (2016.08); *A23L 33/12* (2016.08); *A23L 33/125* (2016.08); *A23L 33/135* (2016.08); *A23L 33/175* (2016.08); *A23L 33/40* (2016.08); *A61K 9/0056* (2013.01); *A61K 31/198* (2013.01); *A61K 33/06* (2013.01); *A61K 47/26* (2013.01); *A61K 47/44* (2013.01); *A61K 47/46* (2013.01); *A23V 2002/00* (2013.01)

(58) Field of Classification Search
CPC .. A61K 35/744; A23L 33/135; A23V 2002/00
See application file for complete search history.

(56) References Cited

U.S. PATENT DOCUMENTS

2016/0324766 A1    11/2016    Stettler et al.

OTHER PUBLICATIONS

David P. Strachan, Hay fever, hygiene, and household size, Br. Med. J. 1989;299;1259-60, BMJ, United Kingdom.
H. Odkada, C. Kuhn, H. Feillet, and J.F.Bach, The 'hygiene hypothesis' for autoimmune and allergic diseases: an update. Clinical and Experimental Immunology, 2010:160:1-9, British Society for Immunology, United Kingdom, Wiley.
Sameul, J. Arbes, Jr. et al.,Can oral pathogens influence allergic disease?, May 2011, vol. 127, Issue 5, pp. 1119-1127, American Academy of Allergy, Asthma & Immunology, Elsevier Inc., US.
Cliff Shunsheng Han, A specific hygiene hypothesis, Medical Hypotheses 93 (2016) 146-149, Elsevier Inc., US.
A. Tedeschi et al., Clinical Exp. Allergy, 2003, 33:449, 454, Blackwell publishing, Oxford, England.

(Continued)

Primary Examiner — Andrew S Rosenthal
(74) Attorney, Agent, or Firm — Caldwell Intellectual Property Law

(57) ABSTRACT

A formulated oral prebiotic edible composition includes a free amino acid containing ingredient comprising L-arginine, the L-arginine comprising free individual molecules of L-arginine, the free individual molecules of L-arginine L present at a concentration of greater than about 0.1 weight percent, a carrier, and a sugar comprising at least one of a monosaccharide and disaccharide, at least two distinct live lactic acid probiotics, wherein one is a lactic acid producing bacterium, and one is a lactic acid fermenting bacterium, wherein the composition is in configuration suitable to be maintained substantively dissolved within the oral cavity, and wherein the composition is in an effective amount to selectively promote stimulation of a first oral microbiota to produce an excretion product, and wherein a second oral microbiota metabolizes the excretion product to treat the respiratory allergic condition and/or an oral and/or sinus infection.

20 Claims, No Drawings

(56) References Cited

OTHER PUBLICATIONS

Caelos A. Cuello-Garcia et al., Probiotics for the prevention of allergy: A systematic review and meta-analysis of randomized controlled trials, Oct. 2015 vol. 136, Issue 4, pp. 952-961, American Academy of Allergy, Asthma & Immunology, Elsevier Inc., US.

Hosana G. Rodrigues et al., Fatiyacids as modulators of neutrophil recruitment, function and survival, European Journal of Pharmacology 785(2016),50-58, Elsevier Inc.,US.

Renan Oliveira Correa et al., Regulation of Immune cell function by short-chain fatty acids, Clinical & Translational Immunology (2016) 5, e73; doi:10.1038/cte.2016.17 & 2016 Australasian Society for Immunology Inc., Campinas, São Paulo, Brazil.

Ken Kikuchi et al., Comparison of Phenotypic Characteristics, DNA-DNA Hybridization Results, and Results with a Commercial Rapid Biochemical and Enzymatic Reaction System for Identification of Viridans Group Streptococci, Journal of Clinical Microbiology, May 1995, p. 1215-1222, American Society for Microbiology, US.

Alan I., Coykendall, Classification and Identification of the Viridans Streptococci, Clinical Microbiology Reviews, Jul. 1989, p. 315-328, American Society for Microbiology, US.

Jessica E. Koopman et al.,Stability and Resilience of Oral Microcosms Toward Acidification and Candida Outgrowth by Arginine Supplementation, Microb Ecol (2015) 69:422-433, Springer Science+Business Media New York 2014.

J.A. Durant et al., Comparison of Batch Culture Growth and Fermentation of a Poultry Veillonella Isolate and Selected *Veillonella* Species Grown in a Defined Medium , Anaerobe (1997) 3, 391-397,1997 Academic Press, US.

Jessica E. Koopman et al., Changes in the oral ecosystem induced by the use of 8% arginine toothpaste, Archives of Oral Biology 73 (2017) 79-87, 2016 Elsevier Ltd, US.

Ethan Kolderman et al., L-Arginine Destabilizes Oral Multi-Species Biofilm Communities Developed in Human Saliva, PLOS ONE | DOI:10.1371/journal.pone.0121835 May 6, 2015.

COMPOSITION FOR A FORMULATED ORAL PREBIOTIC EDIBLE COMPOSITION

CROSS-REFERENCE TO RELATED APPLICATIONS

This application is a continuation-in-part of non-provisional application Ser. No. 16/519,909 filed on Jul. 23, 2019 and entitled "ORAL MICROBIOTA COMPOSITION FOR ORAL AND/OR SINUS INFECTIONS," the entirety of which is incorporated herein by reference. This application is a continuation-in-part of non-provisional application Ser. No. 15/706,323 filed on Sep. 15, 2017, now U.S. Pat. No. 10,398,670 and entitled "ORAL MICROBIOTA PROMOTION FOR ORAL AND/OR SINUS INFECTIONS," the entirety of which is incorporated herein by reference. This application is a continuation-in-part of non-provisional application Ser. No. 15/495,188, filed on Apr. 24, 2017, now U.S. Pat. No. 9,795,579 and entitled "AN ORAL MICROBIOTA PROMOTING COMPOSITION AND METHOD," the entirety of which is incorporated herein by reference.

FIELD OF THE INVENTION

The present invention generally relates to the field of oral cavity microbiota. In particular, the present invention is directed to a formulated oral prebiotic edible composition useful for promoting a desired oral microbiota to treat a respiratory allergic condition and/or oral and/or sinus infection condition in a subject in need of such treatment.

BACKGROUND

In general, the prevalence of allergic diseases has dramatically increased in recent decades and currently affects more than sixty million people in the United States, reducing the quality of life. It is believed and has been found that the presence of certain oral bacteria species/strains may affect the aggressiveness of response of the immune system, for example with respect to allergies. More specifically, while not intending to be bound by any health claims, it is believed that the reduction of normally occurring (commensal) oral bacteria in the normally occurring oral microbiota, for example, by aggressive dental hygiene practices, may serve to make non-pathogenic antigens, such as pollen, more prevalent and visible to the immune system. It is further believed, that as a result, non-pathogenic antigens, such as those related to allergens as well as oral and/or sinus infections may be more readily targeted by the immune system, leading to exacerbated allergic reactions.

For example, oral hygiene hypothesis (OHH) is one aspect of a more general hygiene hypothesis (HH), which was proposed more than two decades ago (see Strachan, D. P. "Hay fever, hygiene, and household size", British Medical Journal 299, 1259-1260 (1989)) to explain the rise in allergic diseases. Numerous scientific studies have since provided support for HH, generally showing a relation between increased exhibition of allergies in association with modern social practices, such as formula infant feeding, antibiotic use, urban living, and reduction in family size (see e.g., Okada, H., Kuhn, C., Feillet, H. & Bach, J. F., "The hygiene hypothesis for autoimmune and allergic diseases: an update" Clin. Exp. Immunol. 160, 1-9 (2010)). Although the molecular mechanisms of immune system modulation by gut microbiota are well understood, efforts to reduce allergic reactions through microbial intervention, such as by the use of probiotics have shown inconsistent results.

Extensive oral hygiene practices, according to oral hygiene hypothesis (Han, C S., "A specific hygiene hypothesis" Med. Hypotheses 2016 August; 93:146-149), are believed to cause the exacerbation of naturally occurring respiratory allergies, such as allergic rhinitis (AR), one of the most common allergic conditions.

There is therefore a need for a composition including an oral cavity microbiota promoting substance and method of using the same that has the effect of promoting a healthy oral microbiota that promotes the healthy operation of the immune system which may have the functional effect of promoting an improved response to allergens as well as oral and/or sinus commensal bacteria, which may be the cause of oral and/or sinus infections.

It is an object of the invention to provide a composition including an oral cavity microbiota promoting substance and method of using the same that has the effect of promoting a healthy oral microbiota that promotes the healthy operation of the immune system which may have the functional effect of promoting an improved response to allergens as well as other oral and/or sinus commensal bacteria, which may be the cause of oral and/or sinus infections.

SUMMARY OF THE DISCLOSURE

In an aspect a formulated oral prebiotic edible composition useful for promoting a desired oral microbiota to treat a respiratory allergic condition and/or oral and/or sinus infection condition in a subject in need of such treatment includes a free amino acid containing ingredient comprising L-arginine, the L-arginine comprising free individual molecules of L-arginine, the free individual molecules of L-arginine L present at a concentration of greater than about 0.1 weight percent, a carrier, and a sugar comprising at least one of a monosaccharide and disaccharide, at least two distinct live lactic acid probiotics, wherein one is a lactic acid producing bacterium, and one is a lactic acid fermenting bacterium, wherein the composition is in configuration suitable to be maintained substantively dissolved within the oral cavity for over a period of at least about 1 minute to about an hour, and wherein the composition is in an effective amount to selectively promote stimulation of a first oral microbiota to produce an excretion product, and wherein a second oral microbiota metabolizes the excretion product to treat the respiratory allergic condition and/or an oral and/or sinus infection.

These and other aspects and features of non-limiting embodiments of the present invention will become apparent to those skilled in the art upon review of the following description of specific non-limiting embodiments of the invention in conjunction with the accompanying drawings.

DETAILED DESCRIPTION

At a high level, aspects of the present disclosure are directed to systems and methods for a formulated oral prebiotic edible composition. In an embodiment, this disclosure can be used to promote a desired oral microbiota to treat a respiratory allergic condition and/or oral and/or sinus infection condition in a subject in need of such treatment. Aspects of the present disclosure can be used to promote stimulation of a first oral microbiota to produce an excretion product. Aspects of the present disclosure can also be used to promote a second oral microbiota to metabolize the excreted product. Aspects of the present disclosure allow for treating a respiratory allergic condition and/or oral and/or sinus infection condition. Exemplary embodiments illustrating aspects of the present disclosure are described below in the context of several specific examples.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. The use of the term "substantially" will be understood to include a value within about 5% of a stated condition or value unless otherwise defined. The use of the term "about" will be understood to include a value within about 5% of a stated condition or value unless otherwise defined. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

It is believed, and has been found that according to the oral hygiene hypothesis (OHH) noted above, that persistent and intensive hygiene practices, together with other life events, such as fever and/or antibiotic usage, will likely change the oral microbiota of an individual. The oral cavity is a complex environment with many different biological niches, such as the tongue, gum, and teeth. Normally occurring microbiota associated with these niches are different and are believed to have a different effect on normal functioning of the immune system.

Likewise, it is believed, and has been unexpectedly found, that the introduction of selected microbiota-promoting substances into the oral cavity in a controlled manner, may promote desired naturally occurring oral bacteria species/strains, which may in turn have an associated effect of modulating or reducing the intensity of certain types of oral and/or sinus infections and/or allergic reactions, including those associated with allergic rhinitis (AR) one of the most common allergic reactions including symptoms such as any combination of a runny or stuffy nose, sneezing, itchy/red eyes, coughing, and congestion.

While not intending to be bound by any particular theory of operation, and making no specific health claims, it is believed that oral microbiota interact with the host largely through metabolites produced by its relevant bacterial members. Those metabolites, such as but not limited to short chain fatty acid, may influence the function of multiple biologic systems and organs, such as the immune system. Missing or severe reduction of the relevant naturally occurring beneficial (commensal) bacteria may cause malfunctioning of the immune system, such as causing over sensitivity to commensal bacteria and/or allergens. Commensal microflora (normal microflora, indigenous microbiota) consists of those micro-organisms, which are present on body surfaces covered by epithelial cells and are exposed to the external environment (gastrointestinal and respiratory tract, vagina, skin, etc.).

Under specific conditions, the commensal bacteria may become opportunistic pathogens and may overcome protective host responses and exert pathologic effects. Therefore, in one embodiment it is believed that the immune system response to the allergens and/or commensal bacteria may be modulated by the method and/or composition such that the associated oral and/or sinus infections and/or allergic reaction symptoms are suppressed relative to what an infection and/or allergic reaction may be with an unhealthy level of, or different commensal microbiota. It is further believed and evidence suggests that over time, as a result of promoting a healthy oral microbiota with selected microbiota-promoting substances that the immune system may function in a healthy manner with a health promoting response to allergens and/or commensal bacteria that have become pathogenic.

Furthermore, due to the connectivity among mouth and respiratory duct and lungs, a healthy oral microbiota may lead to a healthy microbiota in the lungs as well. Eventually the method and/or composition may benefit the healthy functioning of the immune system which may in turn have a healthy response not only to oral and/or sinus infections and/or allergic rhinitis but also the relevant diseases in the lungs, such as asthma.

For example, in other embodiments, the method and/or composition may benefit the healthy functioning of a sensitized immune system with respect to oral and/or sinus infections including airway related infections including but not limited to gingivitis, periodontitis (periodontal disease), tonsillitis, rhinosinusitis, pharyngitis, and laryngitis. While some or a portion of these infections may be caused by pathogen invasion, a sensitized immune system attacking commensal bacteria may lead to the exacerbation and/or cause of infections associated with other opportunistic (pathogenic) commensal bacteria caused infections.

The method and/or composition may be used to promote a healthy functioning of an immune system e.g., by reducing immune system sensitivity by restoring a healthy level of desired commensal bacteria to thereby at least reduce or alleviate symptoms associated with the infections and/or allergens.

In one embodiment, an oral microbiota promoting composition may be provided into an oral cavity that may have the effect of promoting desired microbiota within an oral cavity.

In another embodiment, a method of applying an oral microbiota promoting composition (prebiotic) may be provided that may have the effect of promoting desired microbiota within an oral cavity and have the desired functional effect of treating oral and/or sinus infections including airway infections and/or allergic reaction respiratory conditions including allergic rhinitis.

In one embodiment, a method of applying an oral microbiota promoting composition may include multiple instances of introduction of the composition into the oral cavity (mouth) in the form or a solid, powder, paste, or liquid in the amount of about 1 gm to about 500 gms at one time or multiple times in fractional amounts. Where the oral microbiota promoting composition is in the form of liquid, the method may include dissolving the composition in a liquid.

In another embodiment, a method of applying an oral microbiota promoting composition may include swallowing the composition following introduction of the composition into the oral cavity and following a period of retaining the composition within the mouth for a select period of time including e.g., chewing, gargling, and/or sublimating (dissolving) the composition while within the oral cavity.

In another embodiment, a method of applying an oral microbiota promoting composition may include removing the composition following introduction into the oral cavity by expelling (e.g., pulling out or spitting-out) the microbiota promoting composition following a period of retaining the composition within the mouth.

In another embodiment, a method of applying an oral microbiota promoting composition may include retaining the microbiota promoting composition within the oral cavity from about 10 seconds to about an hour, more preferably, from about 5 minutes to about 30 minutes on a daily basis for a period of about 2 days to about 60 days.

In another embodiment, a method of applying an oral microbiota promoting composition may include introducing the microbiota promoting composition for relatively short periods several times a day, for example from about 1 second to about 30 seconds, each from about 3 to about 10 times a day for a period of about 2 days to about 60 days.

In another embodiment, a method of applying an oral microbiota promoting composition may include extending the periods of introduction of the microbiota promoting composition into the oral cavity, for example, from about every 3 days to about every 10 days, including stopping the introduction of the composition following the disappearance of allergy symptoms.

In another embodiment, a method of applying an oral microbiota promoting composition may include at least partially removing a mucosal film (biofilm) from within the oral cavity prior to or while administering the microbiota promoting composition to the oral cavity.

It will be appreciated that the biofilm may be at least partially removed, including substantially removed (e.g., greater than about 95%), by raising the whole body temperature for a short time, for example, with conventional biological or physical means.

In a related embodiment, the biofilm may be at least partially removed by rinsing out (optionally including scrubbing or rubbing) the oral cavity (mouth) with a heated water containing liquid, such as water, at a temperature of from about 90 to about 130 degrees Fahrenheit prior to applying the oral microbiota promoting composition to the oral cavity. It will be appreciated that rinsing with a hot water containing fluid as noted may advantageously at least partially remove a biofilm from surfaces within the oral cavity, thereby improving the operation of the oral microbiota promoting composition. The oral rinsing may include periodic rinsing, for example, each for about 10 seconds to about 30 seconds over a period of from about 5 to about 15 minutes.

In another embodiment, a method of applying an oral microbiota promoting composition may include at least one of brushing and rubbing portions of the oral cavity with the hot water containing fluid at a temperature of from about 100 to about 130 degrees Fahrenheit including at least the tongue, for example, with at least one of a brush, such as a toothbrush, and/or a wet cloth.

In another embodiment, the oral microbiota promoting composition may be formulated into oral dosage forms such as tablets, caplets, and capsules, or a powder formulation or that may be dissolved in a liquid, for example diluted in a liquid having a ratio of from about 1:1 to about 1:500 with respect to either weight or volume of the liquid (e.g., the liquid being larger number).

In another embodiment, the oral microbiota promoting composition may be formulated or manufactured as a chewing gum or candy, or other edible carrier, for example as an additive having a ratio of from about 1:1 to about 1:500 with respect to either weight or volume of the edible carrier (e.g., larger number). In an embodiment the oral microbiota promoting composition is in a candy configuration. As used in this disclosure a "candy configuration" is a configuration of oral microbiota promoting composition that is made with a sweetener. For example, and without limitation, candy configuration may include one or more chewing gums, hard candies, and the like thereof. In an embodiment, and without limitation, candy configuration may include a lollipop configuration. As used in this disclosure a "lollipop configuration" a candy located at a terminal end of a rod and/or stick/In an embodiment, lollipop configuration may be oriented as a flat and/or rounded candy at the end of a stick. In an embodiment, and without limitation, candy configuration may include a chocolate configuration. As used in this disclosure a "chocolate configuration" is a candy that originates from roasted and/or ground cacao seeds. For example, and without limitation, chocolate configuration may include dark chocolate, milk chocolate, white chocolate, and the like thereof. In another embodiment, candy configuration may include a soft candy configuration. As used in this disclosure a "soft candy configuration" is a candy that is comprised of sucrose esters to enhance and/or increase softness of candy configuration. For example, and without limitation, soft candy configuration may include toffee, fudge, and the like thereof. In another embodiment, and without limitation, candy configuration may include a creamy candy configuration. As used in this disclosure a "creamy candy" is a candy that is comprised of a viscous and/or liquid solution of sweetener in a solvent. For example, creamy candy may include a syrup, molasses, caramel, and the like thereof.

In another embodiment, the oral microbiota promoting composition may be formulated or manufactured as soft candy and/or may include edible food gelling agents such as starch, vegetable pectin, and/or gelatin such as, corn starch, potato starch, carrageenan, and/or any other gelatin.

The addition of gelling agents preferably enables the microbiota promoting composition to be dissolved and released into the oral cavity over an extended period of time.

The gelling agents may be present at a ratio of from about 1:10 to about 1:100 with respect to either weight or volume of the microbiota promoting composition.

For example, in some preferred embodiments, the microbiota promoting composition is formed as a solid and/or gel that may be dissolved relatively slowly over a period of time within the oral cavity to release ingredients that may promote the desired microbiota within the oral cavity over a selected period of time.

It has been found and is expected that the promotion of the desired concentrations of desired microbiota such as *Veillonella* and *Streptococcus* are promoted more effectively to desired concentrations with the oral cavity by a relatively slow release of ingredients within the microbiota promoting composition.

In one embodiment, the microbiota promoting composition may be formed as a solid, gel and/or include gel forming ingredients, so that the ingredients included in a selected dose, capsule or tablet are released from about 50% to about 100% over a period of from about 1 minute to about 60 minutes while being maintained within the oral cavity.

In one embodiment the microbiota promoting composition may be formed as a layered solid, gel and/or gel forming ingredients including layers of different relative concentrations of the microbiota promoting compositional ingredients.

In one embodiment, at least one of one or more of live bacterial ingredients and/or free amino acids may be included with higher relative concentrations in outermost layers, with underlying layers having higher relative concentrations of sugars and other ingredients providing nutrition to the desired microbiota population.

In another embodiment, the oral microbiota promoting composition may be formulated as an additive to an oral hygiene product acting as a carrier, such as toothpaste or mouthwash, the microbiota promoting composition having a ratio of from about 1:1 to about 1:500 with respect to either weight or volume of the oral hygiene product.

In another embodiment, the oral microbiota promoting composition may be provided on bioadhesive delivery devices such as bioadhesive strips that are known in the art. For example, the composition may be provided on or infused into a bioadhesive strip, such as on a bioadhesive or self-adhesive support which supports the composition. For example, the composition may be included in a gel, such as a carbohydrate based gel that may be supported on a solid support, such as a plastic or cross-linked polymer support that may include micro-patterns on a supporting surface (e.g., having spacings of about 0.1 to about 2 mm). The bioadhesive strip infused with or supporting the oral microbiota promoting composition may be self-adhesive (in the presence of oral saliva) to dental or mucosal portions of the oral cavity.

In another embodiment, in a method of manufacturing an oral microbiota promoting composition may be formulated having an edible foodstuff as a carrier, the microbiota promoting composition having a ratio of from about 1:1 to about 1:500 with respect to either weight or volume of the edible foodstuff.

In one embodiment, the desired microbial species/strains promoted in the oral cavity by the oral microbiota promoting composition may be naturally occurring within the oral cavity and/or may be provided separately or within the oral microbiota promoting composition.

In a related embodiment, the desired microbial species/strains may be present in the oral cavity or in the oral microbiota promoting composition at a level of from about 1000 to about 1,000,000,000 living cells.

It will be appreciated that the desired microbial species/strains may be naturally occurring and/or may be obtained commercially and handled in accordance with any applicable safety requirements.

In another embodiment, the desired microbial species/strains promoted in the oral cavity by the oral microbiota promoting composition may include at least a first microbial species that can attach to surfaces (e.g., teeth, tongue, mouth) within the oral cavity and at least one second microbial species that may attach to the same or different surfaces and/or may attach to the at least first microbial species.

In a related embodiment, the at least a first and second microbial species may produce a product, such as a sugar containing moiety, that may be metabolized by the other of the at least a first and second microbial species.

In an embodiment, and without limitation, the oral prebiotic edible composition is configured to selectively promote stimulation of the first oral microbiota to produce an excretion product. As used in this disclosure an "excretion product" is a product and/or chemical that is eliminated from the first oral microbiota. For example, and without limitation, excretion product may include a short chain fatty acid, As a further non-limiting example, excretion product may include a product comprising a sugar moiety. As a further non-limiting example, excretion product may include a lactic acid product. As a further non-limiting example, excretion product may include an adenosine triphosphate product. In another embodiment, a second oral microbiota metabolizes the excretion product to treat the respiratory allergic condition and/or an oral and/or sinus infection condition. For example, and without limitation, the first oral microbiota comprising *Streptococcus* may be selectively promoted to stimulate the production of the excretion product comprising lactic acid, wherein a second oral microbiota, *Veillonella*, may metabolize the lactic acid to produce propionate which may treat the respiratory allergic condition of asthma.

In one embodiment, one of the desired microbial members promoted within the oral cavity promoted by the oral microbiota promoting composition may include one or more live bacterium with lactic acid fermenting capability such as, but not limited to *Veillonella*, which further may include one or more of associated species, such as, but not limited to, *Veillonella* (V.) *dispar* and *Veillonella* (V.) *parvula*.

In one embodiment, one of the desired microbial species/strains promoted within the oral cavity promoted by the oral microbiota promoting composition may include one or more live lactic acid producing bacterium such as but not limited to *Streptococcus* including one or more of associated species, such as, but not limited to, *Streptococcus* (S.) *salivarius* and *Streptococcus* (S.) *thermophilus*.

In a related embodiment, the desired microbial species/strains promoted within the oral cavity by the oral microbiota promoting composition may include at least one live lactic acid producing bacterium and at least one live lactic acid fermenting bacterium such as, but not limited to, respectively, *Veillonella* and *Streptococcus* and their respectively associated preferred species stated above.

In one embodiment, the oral microbiota promoting composition may formulated such that use of a effective amount selectively promotes desired microbial species/strains within the oral cavity such as *Veillonella* and *Streptococcus* by a selected amount. For the selected amount may include a relative concentration (relative to all other types of bacterial species percent within the oral cavity) of from about 5% to about 30%, more preferably, from about 6% to about 20%, even more preferably from about 8% to about 12% of the total amount of the relative types of bacterial present within a sampled area of the oral cavity.

In one embodiment, the oral microbiota promoting composition may be formulated such that use of an effective amount selectively promotes desired microbial species/strains within the oral cavity such as *Veillonella* and *Streptococcus* by a predetermined amount or range. It will be determined that the term effective amount may refer to a pharmaceutically effective amount, e.g., consisting of a pharmaceutical quality of ingredients to achieve a pharmaceutically measurable result.

In another embodiment, an oral microbiota promoting composition is provided that includes at least one amino acid or amino acid containing substance including at least L-arginine. The at least one amino acid may further or alternately include at least one of L-cysteine, DL-aspartic acid, L-glutamic acid, L-serine and L-tyrosine including phosphates, salts, acids, and enzymes comprising the same.

In preferred embodiments, the at least one amino acid may be introduced into the composition including substantially (e.g., greater than about 90%) individual molecules (free amino acids as opposed to amino acid chains) of a respective amino acid, or at least individual molecules of the amino acid L-arginine (free L-arginine).

In some embodiments, the oral microbiota promoting composition may be limited to free L-arginine as the amino acid containing substance.

In another embodiment, the at least one amino acid may be formulated to be substantially decomposed into individual molecules of the amino acid to form free amino acids following introduction into the oral cavity, e.g., during dissolving and/or dissolution of the composition within the oral cavity.

For example, it is believed, and has been observed that L-arginine residues in long or short peptide chains and may not accomplish the promotion of the desired microbiota within the oral cavity, including with the desired health promoting effect, including the promotion of *Veillonella* and *Streptococcus*.

In a related embodiment, the at least one amino acid, may be present in the oral microbiota promoting composition at a weight percent level of from about 0.1 weight percent to about 99.9 weight percent, more preferably, from about 2.5 weight percent to about 95 weight percent, even more preferably from about 20 weight percent to 80 weight percent. In some embodiments the at least one amino acid such as L-arginine may have an upper limit of about 10 weight percent to about 20 weight percent.

In another embodiment, an oral microbiota promoting composition is provided that includes at least one sugar containing substance and at least one amino acid containing substance. The at least one sugar containing substance may include at least one monosaccharide, disaccharide, oligosaccharide, and polysaccharide.

In another embodiment the at least one sugar containing substance may be limited to at least one of one or more monosaccharides and a disaccharides.

In another embodiment the at least one sugar containing substance may be limited to at least one of one or more monosaccharides, disaccharides, and trisaccharides.

Exemplary monosaccharides may include but are not limited to aldohexoses such as but not limited to mannose including associated isomers, phosphates, salts, acids, and enzymes comprising the same.

Exemplary disaccharides may include but are not limited to disaccharides including at least one of galactose and glucose, such as but not limited to lactose, sucrose, melibiose, maltose, cellobiose and trehalose (also known as mycose or tremalose) including associated isomers, phosphates, salts, acids, and enzymes comprising the same.

Exemplary oligosaccharides may include but are not limited to trisaccharides including at least one or more of galactose, glucose, and fructose, such as but not limited to raffinose (also known as melitose), stachyose, and verbascose, including associated isomers, phosphates, salts, acids, and enzymes comprising the same.

Further, Exemplary polysaccharides may include but are not limited to one or more polysaccharide polymers, such as, but not limited to polysaccharides including malotriose units, including but not limited to pullulan, and fructose polymers, such as, but not limited to inulin and further including associated isomers, phosphates, salts, acids, and enzymes comprising the same.

In a related embodiment, the at least one disaccharide may be present in the oral microbiota promoting composition at a weight percent level of from about 0.1 weight percent to about 99.9 weight percent, more preferably, from about 5 weight percent to about 95 weight percent, even more preferably from about 20 weight percent to 80 weight percent.

In a related embodiment, the at least one oligosaccharide may be present in the oral microbiota promoting composition at a weight percent level of from about 0.1 weight percent to about 99.9 weight percent, more preferably, from about 5 weight percent to about 95 weight percent, even more preferably from about 20 weight percent to 80 weight percent.

In a related embodiment, the at least one polysaccharide may be present in the oral microbiota promoting composition at a weight percent level of from about 0.1 weight percent to about 99.9 weight percent, more preferably, from about 5 weight percent to about 95 weight percent, even more preferably from about 20 weight percent to 80 weight percent.

In another embodiment, the oral microbiota promoting composition may include at least one prebiotic fiber. Exemplary prebiotic fibers may include but are not limited to inulin.

In a related embodiment, the at least one prebiotic fiber may be present in the oral microbiota promoting composition at a weight percent level of from about 0.1 weight percent to about 99.9 weight percent, more preferably, from about 5 weight percent to about 95 weight percent, even more preferably from about 10 weight percent to 30 weight percent.

In another embodiment the oral microbiota promoting composition may include additives such as one or more of carbohydrates, amino acids, salts, flavorants, proteins, surfactants, emulsifiers, flavonoids, alcohols, synthetic sweeteners, food preserving agents, and combinations thereof.

In one embodiment, the oral microbiota promoting composition may further include conventional foodstuffs such as one or more of brown sugar, corn syrup, high maltose corn syrup, honey, chocolate, nuts, almonds, spices, cinnamon, cocoa powder, vanilla extract, and vanilla.

In another embodiment, the oral microbiota promoting composition may further comprise a fatty acid. As used in this disclosure a "fatty acid" is a carboxylic acid comprising a hydrocarbon chain and a terminal carboxyl group. For example, and without limitation, a fatty acid may include palmitic acid, stearic acid, oleic acid, caprylic acid, capric acid, lauric acid, myristic acid, arachidic acid, behenic acid, lignoceric acid, cerotic acid, omega-3 fatty acids, short-chain fatty acids, medium-chain fatty acids, long-chain fatty acids, very long chain fatty acids, and the like thereof. In an embodiment, and without limitation, fatty acid may be saturated and/or unsaturated. In another embodiment, the oral microbiota promoting composition may include a hydrogenated coconut oil. As used in this disclosure a "hydrogenated coconut oil" is a coconut oil that has been combined with hydrogen to remove and/or reduce unsaturated bonds. In an embodiment, and without limitation, hydrogenated coconut oil may include a plurality of fatty acids that have been saturated. For example, and without limitation, hydrogenated coconut oil may include one or more caprylic saturated C8 fatty acids, capric saturated C10 fatty acids, lauric saturated C12 fatty acids, myristic saturated C14 fatty acids, palmitic saturated C16 fatty acids, and the like thereof. In another embodiment, the oral microbiota promoting composition may include a triglyceride. As used in this disclosure a "triglyceride" is a chemical comprising an ester derived from glycerol and at least a fatty acid. For example, and without limitation, triglycerides may include medium chain triglycerides, homotriglycerides, heterotriglycerides, and the like thereof.

In another embodiment, the oral microbiota promoting composition may further include a fruit. As used in this disclosure a "fruit" is a seed bearing structure that is formed from the ovary of a flowering plant after flowering. For example, and without limitation, a fruit may include an apple, banana, grape, lemon, orange, strawberry, and the like thereof. In an embodiment, and without limitation, a fruit may include a drupe. As used in this disclosure a "drupe" is an indehiscent fruit structure that comprises an outer fleshy potion that surround a single shell of hardened endocarp with a seed inside. For example, and without limitation, a drupe may include an apricot, olive, loquat, peach, plum, cherry, mango, pecan, and the like thereof. In an embodiment, and without limitation, a drupe may include a nut such as, but not limited to, a cashew, an almond, and the like thereof.

In another embodiment, the oral microbiota promoting composition may further include extract from fruits, such as jujube fruit extract which may include one or more of rhamnose, xylitol, arabitol, fructose, glucose, inositol, sucrose, and maltose.

In another embodiment, the oral microbiota promoting composition may further include a mineral supplement. As used in this disclosure a "mineral supplement" is a chemical element required as an essential nutrient by organisms to perform necessary functions for life. For example, and without limitation, mineral supplements may include vitamins, salts, and the like thereof. As a further non-limiting example, mineral supplements may include calcium, phosphorous, potassium, sodium, magnesium, and the like thereof. As a further non-limiting example, mineral supplements may include salts such as a salt of calcium, lactic acid, and/or gluconic acid such as but not limited to calcium lactate gluconate. As a further non-limiting example, mineral supplements may include sulfur, iron, chlorine, cobalt, copper, zine, manganese, molybdenum, iodine, selenium, and the like thereof.

In a specific exemplary embodiment, an example of making an edible Foodstuff oral microbiota promoting composition is provided below in Example 1:

Example 1:
1 cup raffinose
1 cup trehalose
2 tablespoons mannose
1 cup lactose
½ cup maltose
½ cup L-arginine
2 tablespoons pullulan
1 cup inulin
1 cup dark brown sugar
½ cup corn syrup
½ cup honey
1 cup milk chocolate
1 cup chocolate chips
¼ cup toasted almonds (small chips)
¼ tablespoon cinnamon
¼ tablespoon vanilla extract In one embodiment, the above ingredients may be admixed and heated to a temperature sufficient to melt or liquefy, preferably avoiding boiling for an extended period and then poured into a container to cool.

In another embodiment, live bacterium, in accordance with safety requirements or limitations, may be added following cooling (e.g., as a coating). It will be appreciated that adding the bacterium may be limited by applicable safety precautions and may reduce the shelf life of the product.

Although the embodiments of this disclosure have been described with respect to certain exemplary embodiments, it is to be understood that the specific embodiments are for purposes of illustration and not limitation, as other variations will occur to those of skill in the art.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve compositions and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A formulated oral prebiotic edible composition useful for promoting a desired oral microbiota to treat a respiratory allergic condition and/or an oral and/or sinus infection condition in a subject in need of such treatment, the oral prebiotic comprising:
a free amino acid containing ingredient comprising L-arginine, the L-arginine comprising free individual molecules of L-arginine, the free individual molecules of L-arginine L present at a concentration of greater than about 0.1 weight percent;
a carrier, and a sugar comprising at least one of a monosaccharide and disaccharide;
at least two distinct live lactic acid probiotics, wherein one is a lactic acid producing bacterium, and one is a lactic acid fermenting bacterium;
wherein the composition is in a configuration suitable to be maintained substantially dissolved within the oral cavity for over a period of at least about 1 minute to about an hour, and wherein the composition is in an effective amount to selectively promote stimulation of a first oral microbiota to produce an excretion product, and wherein a second oral microbiota metabolizes the excretion product to treat the respiratory allergic condition and/or an oral and/or sinus infection condition.

2. The composition of claim 1, wherein the excretion product comprises a short chain fatty acid.

3. The composition of claim 1, wherein the excretion product includes a sugar moiety.

4. The composition of claim 1, wherein the composition is in a candy configuration.

5. The composition of claim 4, wherein the candy configuration includes a lollipop configuration.

6. The composition of claim 4, wherein the candy configuration includes a chocolate configuration.

7. The composition of claim 4, wherein the candy configuration includes a soft candy configuration.

8. The composition of claim 4, wherein the candy configuration includes a creamy candy configuration.

9. The composition of claim 1, wherein the oral prebiotic further comprises a conventional foodstuff.

10. The composition of claim 9, wherein the conventional foodstuff includes a cocoa powder.

11. The composition of claim 9, wherein the conventional foodstuff includes a honey.

12. The composition of claim 9, wherein the conventional foodstuff includes a cinnamon.

13. The composition of claim 9, wherein the conventional foodstuff includes a vanilla extract.

14. The composition of claim 9, wherein the conventional foodstuff includes a corn syrup.

15. The composition of claim 1, wherein the oral prebiotic further comprises a fatty acid.

16. The composition of claim 1, wherein the oral prebiotic further comprises a hydrogenated coconut oil.

17. The composition of claim 1, wherein the oral prebiotic further comprises a mineral supplement.

18. The composition of claim 17, wherein the mineral supplement includes a calcium lactate gluconate.

19. The composition of claim 1, wherein the oral prebiotic further comprises a fruit.

20. The composition of claim 19, wherein the fruit includes a drupe.

* * * * *